(12) United States Patent
Hardee et al.

(10) Patent No.: US 10,540,483 B2
(45) Date of Patent: Jan. 21, 2020

(54) PERSONALIZED TRAINING BASED ON PLANNED COURSE AND PERSONAL ASSESSMENT

(71) Applicant: International Business Machines Corporation, Armonk, NY (US)

(72) Inventors: Christopher J. Hardee, Raleigh, NC (US); Steven R. Joroff, Tokyo (JP); Kathy A. McGroddy-Goetz, Fairfield, CT (US); Pamela A. Nesbitt, Ridgefield, CT (US); Scott E. Schneider, Rolesville, NC (US)

(73) Assignee: International Business Machines Corporation, Armonk, NY (US)

( * ) Notice: Subject to any disclaimer, the term of this patent is extended or adjusted under 35 U.S.C. 154(b) by 65 days.

(21) Appl. No.: 15/496,154

(22) Filed: Apr. 25, 2017

(65) Prior Publication Data
US 2018/0307800 A1 Oct. 25, 2018

(51) Int. Cl.
*G06F 19/00* (2018.01)
*A63B 24/00* (2006.01)

(52) U.S. Cl.
CPC ...... *G06F 19/3481* (2013.01); *A63B 24/0075* (2013.01)

(58) Field of Classification Search
CPC .................. A63B 24/0075; G06F 19/3481
See application file for complete search history.

(56) References Cited

U.S. PATENT DOCUMENTS

| 4,817,940 | A | 4/1989 | Shaw et al. |
| 4,907,795 | A | 3/1990 | Shaw et al. |
| 7,771,320 | B2* | 8/2010 | Riley ............... A63B 24/0006 482/9 |
| 7,946,958 | B2 | 5/2011 | Wu |
| 8,275,803 | B2 | 9/2012 | Brown et al. |
| 9,151,616 | B1* | 10/2015 | Henderson ............ G01C 21/00 |

(Continued)

OTHER PUBLICATIONS

"Create Race Map", Race Entry, https://www.raceentry.com/create-race-map, accessed from the Internet on Aug. 8, 2016, 3 pages.

(Continued)

*Primary Examiner* — Eddy Saint-Vil
(74) *Attorney, Agent, or Firm* — Stephen J. Walder, Jr.; Ryan G. Lewis

(57) ABSTRACT

Mechanisms are provided for implementing a personalized training recommendation system. A request is received from a user to generate a personalized training regimen for a specified athletic event and event information is identified comprising characteristics of one or more geographical segments of the specified athletic event. Based on the event information, one or more portions of a geographical region are identified that approximate one or more characteristics of the one or more geographical segments within a predetermined tolerance. A training course is generated at least by combining a selected set of the portions of the geographical region based on an evaluation of a level of matching, for each portion, of characteristics of the portion to the one or more physical characteristics associated with the one or more geographical segments of the specified athletic event, which is then presented to the user as the personalized training regimen for the user.

20 Claims, 6 Drawing Sheets

(56) References Cited

U.S. PATENT DOCUMENTS

| | | | | |
|---|---|---|---|---|
| 2003/0151554 | A1* | 8/2003 | McCarthy | A63B 24/0021 342/450 |
| 2006/0228681 | A1 | 10/2006 | Clarke | |
| 2009/0047644 | A1 | 2/2009 | Mensah et al. | |
| 2009/0287678 | A1 | 11/2009 | Brown et al. | |
| 2010/0273610 | A1 | 10/2010 | Johnson | |
| 2010/0317489 | A1 | 12/2010 | Flaction | |
| 2011/0003665 | A1* | 1/2011 | Burton | G04F 10/00 482/9 |
| 2011/0066587 | A1 | 3/2011 | Ferrucci et al. | |
| 2011/0125734 | A1 | 5/2011 | Duboue et al. | |
| 2012/0047102 | A1* | 2/2012 | Petersen | G06Q 30/0282 706/52 |
| 2012/0253488 | A1* | 10/2012 | Shaw | G06Q 10/04 700/91 |
| 2012/0283855 | A1* | 11/2012 | Hoffman | G01C 21/20 700/91 |
| 2013/0007055 | A1 | 1/2013 | Brown et al. | |
| 2013/0018652 | A1 | 1/2013 | Ferrucci et al. | |
| 2013/0066886 | A1 | 3/2013 | Bagchi et al. | |
| 2013/0138734 | A1 | 5/2013 | Crivello et al. | |
| 2014/0107816 | A1* | 4/2014 | Guedalia | G06F 19/3481 700/91 |
| 2014/0114450 | A1 | 4/2014 | Martin | |
| 2014/0342329 | A1 | 11/2014 | Debenedetto et al. | |
| 2014/0378870 | A1* | 12/2014 | Barduson | A61B 5/1075 600/587 |
| 2015/0087478 | A1* | 3/2015 | Zhang | A63B 24/0003 482/8 |
| 2016/0209225 | A1 | 7/2016 | Nagy et al. | |
| 2016/0263439 | A1* | 9/2016 | Ackland | G06F 19/3481 |

OTHER PUBLICATIONS

"Samsung Announces a New Smart Biometric Processor for the Mobile Market", TweakTown website, http://www.tweaktown.com/pressrelease/10265/samsung-announces-new-smart-biometric-processor-mobile-market/index.html, Dec. 31, 2015, 4 pages.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J. Res. & Dev. vol. 56 No. 3/4 Paper 3, May/Jul. 2012, pp. 3:1-3:15.

Saab, "ManPack300: Deploying the Future in Live Training", http://saab.com/globalassets/commercial/land/training-and-simulation/live-training/manpack300/manpack-300_web.pdf, Dec. 2, 2014, 6 pages.

Watson, Lance, "6 Key Workouts to Prepare for Your IRONMAN 70.3", TrainingPeaks, http://home.trainingpeaks.com/blog/article/6-key-workouts-to-prepare-for-your-ironman-70-3, May 5, 2016, 4 pages.

Watson, Lance, "How to Simulate Your IRONMAN Bike", TrainingPeaks, http://home.trainingpeaks.com/blog/article/how-to-simulate-your-ironman-bike, Apr. 9, 2015, 4 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

List of IBM Patents or Patent Applications Treated as Related, Nov. 7, 2017, 2 pages.

* cited by examiner

PERSONALIZED TRAINING BASED ON PLANNED COURSE AND PERSONAL ASSESSMENT

BACKGROUND

The present application relates generally to an improved data processing apparatus and method and more specifically to mechanisms for personalizing training based on a planned course and individual personal assessment.

Athletes and other individuals that participate in athletic events or even personal physical training, typically perform training in gyms using specialized training equipment. In addition, for some physical training, the training may take place in various physical environments, such as in the case of training of a race, a marathon, an obstacle course, or the like. For example, a bicyclist or runner may train by riding their bicycle or running in areas of their physical environment, e.g., along a route or track.

The training is generally directed to helping the individual increase their endurance, strengthen the individual, increase lung capacity, become faster, and the like, in a generalized manner. Even custom training regimens, or working with a training expert one on one, will focus on general areas of weakness of the individual.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising at least one processor and at least one memory, the at least one memory comprising instructions executed by the at least one processor to cause the at least one processor to implement a personalized training recommendation system. The method comprises receiving, by the personalized training recommendation system, a request from a user to generate a personalized training regimen for a specified athletic event and identifying, by the personalized training recommendation system, event information comprising characteristics of one or more geographical segments of the specified athletic event. The method also comprises identifying, by the personalized training recommendation system based on the event information, from a knowledge base, one or more portions of a geographical region that approximate one or more characteristics of the one or more geographical segments associated with the specified athletic event within a predetermined tolerance. Moreover, the method comprises generating, by the personalized training recommendation system, a training course at least by combining a selected set of the portions of the geographical region based on an evaluation of a level of matching, for each portion, of characteristics of the portion to the one or more physical characteristics associated with the one or more geographical segments of the specified athletic event. In addition, the method comprises presenting, by the personalized training recommendation system, the generated training course to the user as the personalized training regimen for use by the user in preparing for the specified athletic event.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
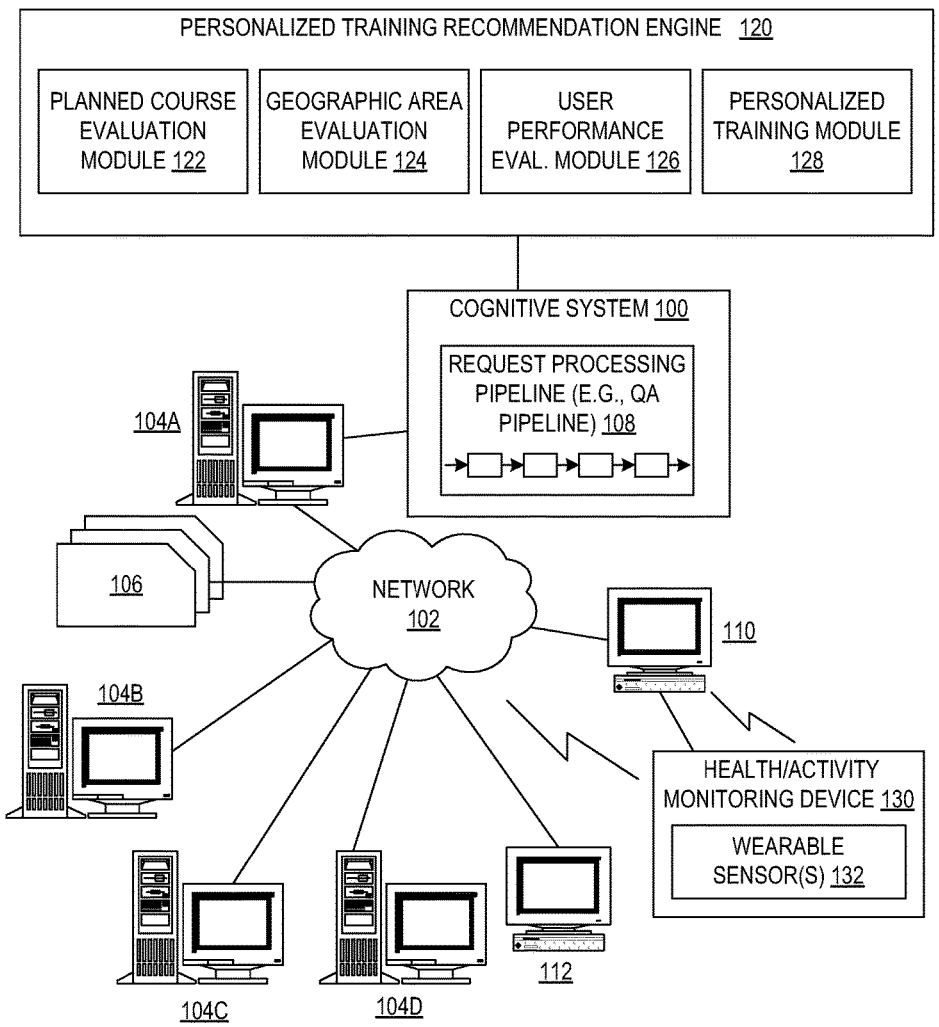
FIG. 1 depicts a schematic diagram of one illustrative embodiment of a cognitive system in a computer network.

The illustrative embodiments provide mechanisms for personalizing training based on a planned course or athletic event and individual personal assessments of strengths and weaknesses relative to the physical requirements of the planned course or athletic event. The mechanisms of the illustrative embodiments focus on the particular course or athletic event that an individual wishes to train for, and the individual's capabilities and weaknesses with regard to that athletic event. Based on this information, the mechanisms of the illustrative embodiments determine areas where the individual needs to focus training to increase their capabilities with regard to the demands of the athletic event. In addition, the mechanisms of the illustrative embodiments find real world physical locations within a given proximity of the individual where the physical locations provide similar physical features to that of the course or athletic event and that will strengthen the individuals' capabilities with regard to areas where the individual needs to focus training.

The illustrative embodiments utilize a cognitive computing system to analyze the physical features and other characteristics of the course or athletic event, e.g., weather conditions, timing of the athletic event, surface type, length, hill density and elevations or grades, altitudes, etc. and correlates those physical features and characteristics with similar characteristics of geographical areas near the individual that is being trained for the athletic event, or otherwise within a geographic region specified by the individual.

Portions of geographical areas that are similar in characteristics may be selected to generate a training course for the training of the individual for the athletic event. The individual's performance on the training course may be monitored and areas of weakness or insufficient performance may be identified. A training regimen for strengthening the areas of weakness or insufficient performance may then be generated. In addition, the process may be repeated to identify portions of geographical areas that have characteristics that will assist the individual in addressing the areas of weakness or insufficient performance so that a modified training course may be generated.

The athletic event may be any athletic event in which an individual may be required to expend physical efforts to accomplish completion of the athletic event and for which physical training is to be performed. Examples of such athletic events may include, for example, marathons, triathlon, bicycle races, crewing competitions, sailing competitions, various running races, or any other athletic event requiring physical training of the individual. For purposes of the following description a bicycling race will be used as an exemplar for illustrating the operation of the mechanisms of the illustrative embodiments.

With the mechanisms of the illustrative embodiments, assume that an individual, or user, is preparing for a bicycling race, such as the Tour de France, Giro d'Italia, Vuelta a Espana, or the like, that is at a specific location, on a specific date, with a specific course and which has been participated in by others previously. A cognitive system ingests data regarding the course, e.g., the terrain, the environmental characteristics (elevation, standard humidity, air quality, temperatures, light levels, roughness of the course, curvature of the course surface (which may be especially important in running races, etc.), and the like, to thereby characterize the course with regard to a plurality of different geographical and environmental condition characteristics. The cognitive system further ingests similar data regarding a geographical area designated by the user and/or associated with a user's geographic location. For example, a user selectable range value may indicate a geographical range about a user's home geographical location for which data is to be ingested by the cognitive system.

For example, assume the user is located in the United States of America but wants train for the Tour de France and wants to emulate the conditions of the Tour de France as part of the user's training. The user may designate a geographical region which the user is willing to consider for identification of training courses to assist the user in emulating the conditions of the Tour de France in the United States of America. This geographical region may be specified with regard to a range or proximity to the user's home location, e.g., 100 mile radius around a user's home location or may be a separate geographical region indicating areas where the user is willing to travel in order to perform their training. The cognitive system analyzes the geographical and environment condition information for the athletic event or course, i.e. Tour de France in this example, and analyzes the geographical and environment condition information for the user specified geographic region to identify geographical areas within the geographical region that have similar geographical and/or environmental conditions to that of the athletic event.

In addition, the cognitive system ingests personal data about the user including data regarding the user's previous performance on similar types of courses or in similar athletic events (e.g., other bicycle races, bicycling events, or the like in the above example, demographic information (e.g., age, gender, etc. which may be used to compare the user with other users of similar demographics for purposes of identifying desired performance levels, areas where similar users had difficulty on a course, or the like), as well as health information including physical attributes, measurements of fitness and physical capabilities, and the like. This personal data about the user may also include health information obtained from sensors associated with the user, such as wearable sensors, e.g., FitBit, instrumented clothing, heart rate monitors, biometric processing units and sensors, or other wearable activity/health sensor. This personal health information may include such information as previous measurements of the user with regard to fitness and strain level during performance of physical activities. For example, sports medicine facilities, hospitals, doctors offices, and the like, may make use of various types of medical equipment to measure various aspects of the user's personal health and record that information into data structures in medical computing systems. This data may be provided as part of a corpus of information that is ingested by the cognitive system along with other data from the wearable activity/health sensors, data entered manually by a health provider or the user, or the like. Any source of personal health information about the user may be included as a source of data provided in a corpus of information.

The cognitive system also ingests data regarding medical and/or athletic domains as resource information that may be utilized to perform cognitive operations as described hereafter. For example, the cognitive system ingests data from physical therapy and sports medicine journals that comprise content recommending methods for improving human capabilities, such as improving frailty or weakness in various physical performance areas. The resource information may further comprise information from other medical and/or athletic sources including the American medical association (AMA), the American Medical Society for Sports Medicine (AMSSM), National Athletic Trainer's Association (NATA), various physician's desk reference texts, medication texts, and/or any other source of information that may be pertinent to the physical training of a user for a particular athletic event or course.

The user may submit a query to the cognitive system to find a training course which emulates, as close as possible, the race course, or other athletic event, in terms of length, geographical characteristics, and environment characteristics, e.g., elevation, proximity of hills relative to one another, number of hills per unit mile (i.e. hill density), types of road or course path conditions, weather, lighting levels, temperature, etc. The cognitive system selects portions of the geographical area in the geographical region specified by the user, e.g., within 100 miles of the user's home location, that provide similar characteristics to those of portions of the race course or athletic event, if possible. The portions of the geographical area in the geographical region need not be contiguous, however contiguous portions, or portions that are relatively closer to one another than others, may be preferred over others. The identified portions are output to the user as a suggested training course for the identified athletic event or race course for which training is to be performed. In outputting these identified portions, the portions may be connected to one another, such as by including intervening portions of the geographical area that connect the identified portions, to generate a contiguous training course if desired, however in doing so some portions of the training course may not match the conditions of the athletic event or race course for which training is to be performed.

The user then performs training on the identified real world physical training course that emulates the race course or athletic event, while wearing health and/or activity monitoring equipment that is capable of providing data to the cognitive system regarding the user's performance while training on the training course. The user's performance data while training on the identified training course may be correlated, such as via global positioning system (GPS) capabilities, cellular triangulation, or other location determining capabilities of electronic equipment, with portions of the training course to correlate the user's performance with regard to particular characteristics of the training course. In addition to the wearable health and/or activity monitoring equipment data, the cognitive system may obtain data regarding the user's performance during training on the training course from medical personnel, the user himself/ herself, or the like, such as through manual entry of such information, responses to a questionnaire presented after training, evaluation of the user via medical equipment after training on the training course, or any other methodology for obtaining data regarding the user's performance and/or health condition after training.

For example, through the operation of the cognitive system, portions of a geographic area with 50 miles of the user's home location may be identified in which a subset of the geographical and/or environmental characteristics of the athletic event, e.g., the Tour de France, are closely matched using a fuzzy matching approach. These portions may be similar in elevation, humidity levels, temperature, frequency of hills, course terrain type, etc., where "similarity" may be determined as a match within a given acceptable tolerance value of the actual values associated with the race course or athletic event for which training is being performed. The portions of the geographical area may be pieced together by including intervening portions of the geographical area such that a contiguous training course is generated. The user may then train on that training course, such as by bicycling on the training course, for example, while wearing health and/or activity monitoring equipment that is able to record and/or transmit data representing the health and/or activity of the user while training on the training course. The user may also be treated after training by a medical professional, sports trainer, or other professional with the use of medical equipment to determine the health status of the user after training. Furthermore, the user and/or medical professional may manually enter information indicating aspects of the user's training on the training course and/or health. All of this performance and/or health data may be provided as part of a corpus of information ingested by the cognitive system.

Thus, for example, the wearable sensor information may indicate the user's heart rate at various points during the training course, the pedaling rate or speed of the bicycle at various points during the training course, the user's blood pressure, breathing rate, and the like, during various points of the training course. This information may be correlated with the locations along the training course where the particular performance and/or health data was obtained by the wearable sensors. The information gathered after training may also be utilized as a more general performance and/or health data for the training course as a whole.

The performance and/or health data obtained is analyzed by the cognitive system to correlate observed stress/strain and/or low performance or weaknesses with types of motions used at various portions of the training course. These types of motions may then be used to identify exercises or training regimens that the user may implement to strengthen the user's capabilities in these areas of weakness or insufficiency in performance with regard to specific elements of the training course in question and thus, the ultimate course or athletic event. These training regimens or exercises may comprise both training regimens and exercises with regard to the real world physical training course, exercises and/or training activities performed in a gym or with more stationary gym equipment, exercises and/or training activities the user can perform off the training course and outside of a gym environment, and/or the like.

In some cases, a new analysis of the geographical area in the geographical region specified by the user may be performed to identify portions of the geographical area that have characteristics that will assist the user in strengthening the areas of weakness or insufficiency in performance. For example, if it is determined that the user seems to have difficulty on hilly terrain and needs to increase the lung capacity, endurance, and/or strength with regard to hilly terrain, then the training course may be modified to emphasize hilly areas that will assist the user in building up the user's performance with regard to hilly areas. Moreover, the geographical region may be analyzed to identify other portions of geographical areas that may not have been previously present in the training course, to thereby add those portions to the training course to emphasize hilly areas as part of the training course. These additions may also replace other portions in the training course for which the user has shown sufficient performance. Thus, a modified training course may be generated in addition to, or in replacement of, the training regimens and/or exercises mentioned above.

It should be appreciated that the evaluation of weaknesses as well as how to strengthen those areas as well as increase performance may make use of the ingested data regarding sports medicine and the like. Moreover, it should be appreciated that in some illustrative embodiments, analysis of data associated with other users that have overcome the identified areas of weakness or performance insufficiency may be performed by the cognitive system to determine the training regimen and/or types of courses or characteristics of portions of geographical areas that were used to assist those users in overcoming such weakness or performance insufficiency. This information may be used along with other reference information to determine the optimum training regimen and/or portions of geographical areas that will assist the present user in strengthening the areas of weakness and improve performance.

Thus, the present illustrative embodiments provide mechanism that focuses a user's training on areas of weakness or insufficient performance that are specific to the particular race course or athletic event that the user is training for. Moreover, the training is customized to the particular user and the particular race course or athletic event such that a training course, training regimen, and/or set of exercises are focused on assisting the user in strengthening areas of weakness and/or insufficient performance of the particular user with regard to the particular demands of the race course or athletic event that the user is training for.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for personalizing training based on a planned course or athletic event and individual personal assessments of strengths and weaknesses relative to the physical requirements of the planned course or athletic event. The illustrative embodiments utilize cognitive systems which employ one or more specially configured computing devices and/or data processing systems to perform various operations for ingesting information, analyzing that information, and performing cognitive operations based on the ingestion and analysis. These operations are not routine operations performed by a computing device, but require higher levels of functionality which involve implementation of specialized hardware and/or software that implement a type of artificial intelligence with regard to the ingested information.

Figure 2:
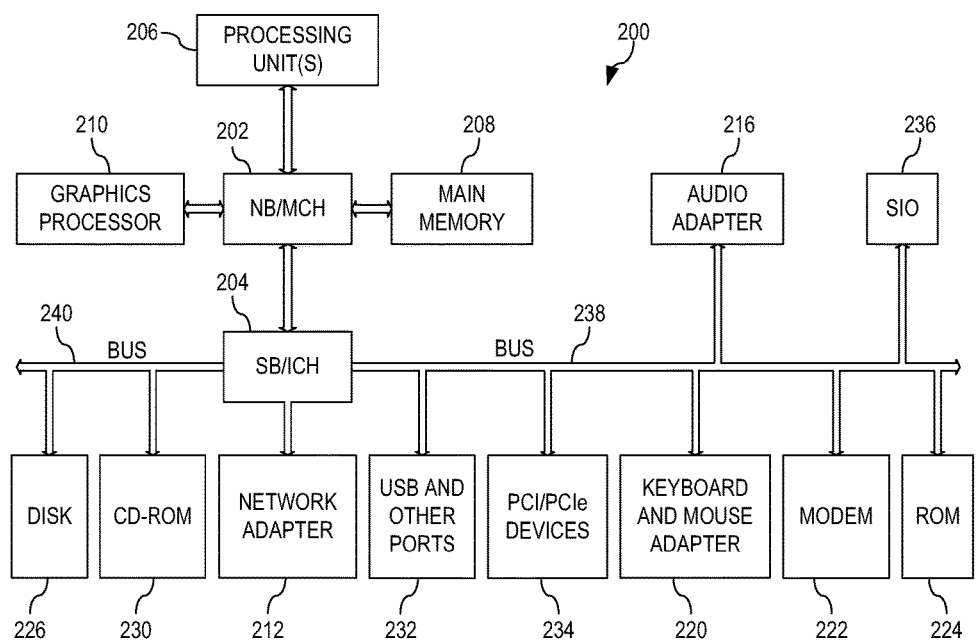
FIG. 2 is a block diagram of an example data processing system in which aspects of the illustrative embodiments are implemented.

It should be appreciated that, with the illustrative embodiments being specifically directed to computer based mechanisms for improving the physical training of athletes and/or other users with regard to a particular race course or athletic event, the illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for providing personalized physical training based on a planned course and/or athletic activity and an individual assessment of the user being trained. The cognitive system, in some illustrative embodiments, as shown in FIGS. 1-3, implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the cognitive system. As described in more detail hereafter, the particular application that is implemented in the cognitive system of the present invention is an application for identifying a physical geographical area, or portions thereof, that match (within a given tolerance) the geographic and environmental characteristics of a planned course or athletic event such that a user may perform physical training on a training course generated by the concatenation or other combination of the portions of the physical geographical area. The cognitive system further provides mechanisms for analyzing a user's performance during training on the generated training course and, based on results of this analysis, determine a training regime, exercises, and even modify the training course to focus on areas of weakness or insufficient performance so as to strengthen the user in these areas.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to identifying a matching geographical area for generating a training course while a second request processing pipeline may be directed to evaluating the user's performance, health metrics, and the like, so as to generate a training regime, exercise recommendation, or even modify a training course based on areas of identified weakness or insufficient performance.

Moreover, each request processing pipeline may have their own associated corpus or corpora that they ingest and operate on, e.g., one corpus for medical and/or athletic training resource documents, another corpus for geographical and/or environmental information for various geographic areas as well as for known courses and athletic events, and another corpus for user health and athletic performance information. In some cases, the request processing pipelines may each operate on the same domain of input questions but may have different configurations, e.g., different annotators or differently trained annotators, such that different analysis and potential answers are generated. The cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "Where should I train for the Tour de France?", the cognitive system may instead receive a request of "generate a training course for the Tour de France," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a cognitive system with regard to obtaining geographic and/or environmental characteristic information for a planned course or athletic event, geographic and/or environmental characteristic information for a user specified geographic region, identify geographic areas, or portions thereof, in the user specified geographic region that match (within a tolerance) the characteristics of the planned course or athletic event, and generate a training course for the user that indicates a real world physical geographical course the user can train on that has portions of the training course that represent the actual planned course or athletic event that the user wishes to train for. Moreover, the illustrative embodiments augment and extend the functionality of the cognitive system to evaluate a user's actual performance while training on the generated training course, as well as other health information gathered from the user, health data sources, treating medical professionals, and the like, to generate training regimens, exercises, and/or modify the training course to help the user improve in areas where weakness or insufficient performance is identified.

In view of the above, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language Deduce various language specific or agnostic attributes from natural language High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of personalized training of a user for a designated planned course or athletic event, this analysis may involve processing geographical and/or environmental information from various sources as provided in a corpus of documentation or information, to identify matching portions of geographical and/or environmental information in geographic areas within a user designated geographic region. Moreover, this analysis by the cognitive system may involve analyzing a user's health records, health and/or performance metrics as obtained from wearable sensors, analysis of medical and/or athletic training resource documentation, and the like, to identify areas of weakness or insufficient performance, training regimens and exercises to perform to strengthen the user in areas of weakness or insufficient performance, and/or modify a training course to focus on these areas of weakness or insufficient performance.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a personalized training recommendation engine 120. The personalized training recommendation engine 120 provides personalized training based on a planned course or athletic event and individual personal assessments of strengths and weaknesses relative to the physical requirements of the planned course or athletic event. The personalized training recommendation engine 120, while shown as a separate entity in FIG. 1 for illustration purposes, may in fact be integrated into the logic of the cognitive system 100 and/or request processing pipeline 108.

As shown in FIG. 1, the personalized training recommendation engine 120 comprises a planned course evaluation module 122, a geographic area evaluation module 124, a user performance evaluation module 126, and a personalized training module 128. It should be appreciated that the personalized training recommendation engine 120 may comprise other modules and/or logic not specifically shown in FIG. 1 which perform operations to facilitate or otherwise support the operations associated with the modules 122-128. For example, control logic may be provided in the personalized training recommendation engine 120 which performs functions to orchestrate the interaction of operations by the various modules 122-128. Moreover, communication interface logic may be provided to facilitate communication to/from the personalized training recommendation engine 120.

The cognitive system 100 may receive a request from a user, such as from client computing device 110, to generate a training course for the user for a specified planned course or athletic event. It should be appreciated that in the illustrative embodiment described herein, the planned course or athletic event is one that is well known and for which the geographical location and environmental characteristics are well known, such as the Tour de France, Boston Marathon, etc. However, in other illustrative embodiments, the user may be presented with an interface on their client computing device 110 through which the user may designate, such as in a free form manner, a planned course. For example, there may be athletic events that are newly created, or less well known, for which the planned course may not be well known and thus, the user may need to designate the planned course via the interface. In other cases, the user may wish to define their own planned course that is not affiliated with some previously known athletic event. The designation of the planned course may be performed in any suitable manner, such as by way of user input to a geographic map drawing lines along the planned course to designate the planned course, entry of coordinates indicating the legs of the planned course, or the like. Moreover, the user may specify the time of day, year, and other characteristics defining the planned course via the interface. For purposes of the following description, however, it will be assumed that the planned course or athletic event is well known such that the actual geographic location, timing, and other defining characteristics are well known.

The user request specifies the planned course and defining characteristics of the planned course for which the user wishes to train. For example, the user may designate the Tour de France in the request, e.g., "generate a training course for the Tour de France". Since the Tour de France is a known course and occurs at a known time of the year, the user does not need to designate any further defining characteristics. The designation of the Tour de France may be used by the cognitive system to retrieve from a corpus of information the particular timing information, geographical information of the course, the expected environmental characteristics for that timing and geographical location, etc. for the Tour de France for the next occurrence of the athletic event. In other cases, where the timing of the planned course may be variable, the user may need to designate the timing when the user plans to participate in the athletic event or utilize the planned course.

The request from the user may further specify a geographic region which the user wishes to have considered by the cognitive system when identifying geographic areas that match the characteristics of the planned course or athletic event. For example, the request may specify that the user wishes to have an area having a range of 100 miles around the home location of the user considered. The user may also specify in the request a geographical region of a county, set of counties, state, set of states, territory, set of territories, country, or set of countries, as geographical regions for consideration by the cognitive system. For example, the user may request that the cognitive system 100 look for geographic areas in the state of Texas, or within 100 miles of Dallas, Tex., that match the characteristics of the Tour de France.

The cognitive system 100 receives the user's request, parses it to identify the defining characteristics of the planned course or athletic event and what is being requested, e.g., a training course that matches the planned course or athletic event that is within 100 miles of Dallas, Tex. The cognitive system 100 employs the personalized training recommendation engine 120, which may be integrated into the request processing pipeline 108 or otherwise provided as part of the cognitive system 100, to obtain and analyze the physical features and other geographical and/or environment characteristics of the planned course or athletic event, e.g., weather conditions, lighting level, terrain type, temperatures, humidity levels, oxygen levels (for various elevations), changes in elevation, hills per unit of distance, or any other geographical and/or environmental characteristics that may be pertinent to a user's ability to perform when engaged in the athletic event.

The planned course evaluation module 122 obtains the physical features and geographical and/or environmental characteristics of the planned course or athletic event from the corpus or corpora 106. For example, the planned course evaluation module 122 may utilize the natural language processing and scoring mechanisms of the request processing pipeline 108 to evaluate electronic documents in the corpus 106 to identify and extract such physical features and geographical and/or environmental characteristics for the planned course or athletic event. The planned course evaluation module 122 may analyze the characteristic information obtained to identify characteristics for the particular time when the user plans to engage in the athletic event or planned course, e.g., performing statistical analysis of data obtained from the corpus, such as temperature and/or weather data, to provide a predicted characteristic for the time when the user plans to engage in the athletic event or planned course. As a result, a collection of characteristics, correlated to geographic locations of the planned course or athletic event, is generated.

The resulting collection of characteristics for the planned course or athletic event may be provided to the geographic area evaluation module 124. The geographic area evaluation module 124 correlates those characteristics with geographical areas in the geographical region specified by the user, e.g., a geographical region of a 100 mile radius around Dallas, Tex. in the example above. The geographic area evaluation module 124 may perform a similar obtaining of characteristic data and analysis of that characteristic data from the corpus 106 as performed by the planned course evaluation module 122, however the operation is done for the specified geographic region. As a result, a set of characteristics for the geographic region is obtained. The characteristics are associated with geographical locations within the geographic region such that portions of the geographic region, e.g., geographic areas or portions of geographic areas, may be identified that have matching characteristics to those of the planned course or athletic event. Hence, a first set of characteristics is generated by the planned course evaluation module 122, and a second set of characteristics is generated by the geographic area evaluation module 124.

The geographic area evaluation module 124 then identifies matches between the first set of characteristics (for the planned course or athletic event) and the second set of characteristics (of the specified geographic region). These matches may be fuzzy matches in that they may match within a given tolerance, e.g., 10%, of each other such that a perfect match is not required. The matching may be done with regard to a variety of different characteristics such that different portions of the geographic region may match a different numbers of characteristics for different portions of the planned course or athletic event, e.g., a first portion of the geographic region may match elevation and terrain of a portion of the planned course while a second portion of the geographic region may match a number of hills per unit distance characteristic of the planned course.

Portions of geographical areas in the geographical region, which are similar in characteristics to that of the planned course or athletic event, may be selected to generate a training course for the training of the individual for the planned course or athletic event. The portions of geographical areas may be selected favoring portions that provide a contiguous path or course while also having matching characteristics. For example, if a first portion and a second portion were selected and they form a contiguous path or course, then these would be favored over selection of a first portion and a third portion that is not contiguous with the first portion. In cases where there is a competition or balancing between contiguousness and matching of characteristics, depending on the implementation, one or the other may be weighted or favored more highly, e.g., contiguousness may be more important in one embodiment while in another embodiment matching characteristics may be more important to the generation of a training course. The best matching portions of the geographical areas, i.e. those that have the largest number of matching characteristics or have the highest level of matching with characteristics of the planned course or athletic event, which also have the most contiguous course generation by selection of those portions of geographical areas, will be selected.

It should further be appreciated that in evaluating whether portions are "contiguous" or not, may not require that the portions be adjacent to one another and thus, themselves be contiguous. To the contrary, in some illustrative embodiments, relative distances between portions may be evaluated such that those portions that are closer to one another and thus, can be made contiguous by the addition of other intervening portions, may be more highly weighted than those that are further apart from one another and thus, would require larger or more intervening portions to make a contiguous training course. Hence, evaluation of the relative distances between portions having matching characteristics may be further considered when determining which portions to select for inclusion in a training course.

The geographic area evaluation module 124 takes the selected portions of geographical areas and generates a training course for the user based on a combination of the portions of the geographical areas. This combination of portions of geographical areas may require the concatenation of other portions of geographical areas that do not match or have relatively low levels of matching to the portions selected, with the selected portions of geographical areas so that a contiguous training course is generated that connects the selected portions of geographical areas. This does not mean that the training course needs to be a closed loop, but rather that all of the selected portions are connected in some manner either to other selected portions or via intervening portions that are concatenated to the selected portions. The result is a training course that has selected portions of geographical areas that closely match the characteristics of the planned course or athletic event.

The training course is returned by the cognitive system 100 to the user via the user's computing device 110. The training course may be output to the user via the client device 110 so that the user may be able to perform training on the training course and thereby train for the planned course or athletic event. Moreover, the client computing device 110 may provide the training course information to a health/activity monitoring device 130, which may be a portable or wearable device, which the user may be able to consult while training on the training course, e.g., a smart phone, portable tablet computer, smart watch, wearable health/activity monitor, or the like. The training course information may be output in a graphical manner on the client computing device 110 and/or the health/activity monitoring device 130.

The health/activity monitoring device 130 may comprise or communicate with wearable sensors 132 that monitor various health metrics, biometric metrics, and/or activity metrics, such as motions performed by the user. The user then performs training on the training course while wearing the wearable sensors 132 and/or health/activity monitoring device 130. The wearable sensors 132 collect health monitoring and/or activity monitoring data which may be provided to the cognitive system 100 via the health/activity monitoring device 130 and client computing device 110, or directly from the health/activity monitoring device 130 via the network 102. The health and activity data obtained from the wearable sensors 132 and/or health/activity monitoring device 130 may be correlated, such as via global positioning system (GPS) capabilities, cellular triangulation, or other location determining capabilities of electronic equipment, with portions of the training course to correlate the user's performance with regard to particular characteristics of the training course. In addition to the wearable health and/or activity monitoring equipment data, the cognitive system may obtain data regarding the user's performance during training on the training course from medical personnel, the user himself/herself, or the like, such as through manual entry of such information, responses to a questionnaire presented after training, evaluation of the user via medical equipment after training on the training course, or any other methodology for obtaining data regarding the user's performance and/or health condition after training.

Thus, for example, the wearable sensor information from the wearable sensors 132 may indicate the user's heart rate at various points during the training course, the pedaling rate or speed of the bicycle at various points during the training course, the user's blood pressure, breathing rate, and the like, during various points of the training course. Moreover, wearable sensors 132 may comprise, or communicate with, biometric and/or performance processing or bio-processor devices that process the raw sensor information and generate more complex metrics including, for example, performing bioelectrical impedance analysis (BIA), photoplethysmogram (PPG), electrocardiograph (ECG), skin temperature analysis, galvanic skin response (GSR), and the like which may further be analyzed to measure body fat, skeletal muscle mass, heart rate, heart rhythm, skin temperature, stress level, etc. An example of such a bio-processor is the Samsung Bio-Processor, under development by the Samsung Electronics Co., Ltd. and described in the article "Samsung Announces a New Smart Biometric Processor for the Mobile Market," TweakTown website, Dec. 31, 2015. Various sensor and bio-processor based devices are available to measure a plethora of different user health and performance metrics, any of which, and any combination of which, may be used with the mechanisms of the illustrative embodiments without departing from the spirit and scope of the illustrative embodiments.

This information may be correlated with the locations along the training course where the particular performance and/or health data was obtained by the wearable sensors 132. The information gathered after training may also be utilized as a more general performance and/or health data for the training course as a whole. Combined, this information provides an indication of the user's performance during the training on the training course which, when analyzed, will identify areas where the user is weak or has insufficient performance both with regard to the user's capabilities and with the particular characteristics of the training course, and ultimately the planned course or athletic event that the training course emulates.

In addition, the cognitive system 100 ingests personal data about the user from the corpus 106 including data regarding the user's previous performance on similar types of courses or in similar athletic events, as well as health information including physical attributes, measurements of fitness and physical capabilities, and the like. This personal data about the user may also include previously obtained health and/or activity information obtained from the wearable sensors 132 associated with the user. This personal health and/or activity information may include such information as previous measurements of the user with regard to fitness and strain level during performance of physical activities. For example, sports medicine facilities, hospitals, doctors offices, and the like, may make use of various types of medical equipment to measure various aspects of the user's personal health and record that information into data structures in medical computing systems. This data may be provided as part of the corpus 106 that is ingested by the cognitive system 100 along with other data from the wearable activity/health sensors 132, data entered manually by a health provider or the user, such as via their client computing device 110 and/or a medical professional computing device, or the like. Any source of personal health and/or activity information about the user may be included as a source of data provided in a corpus of information.

The cognitive system 100 also ingests data regarding medical and/or athletic domains from the corpus 106, as resource information that may be utilized to perform cognitive operations, such as identifying particular training regimens, exercises, and training course characteristics, that will assist a user in strengthening their capabilities with regard to areas of weakness or insufficient performance. For example, the cognitive system ingests data from physical therapy and sports medicine journals that are represented electronically in the corpus 106, and which comprise content recommending methods for improving human capabilities, such as improving frailty or weakness in various physical performance areas. The resource information may further comprise information from other medical and/or athletic sources including the American medical association (AMA), the American Medical Society for Sports Medicine (AMSSM), National Athletic Trainer's Association (NATA), various physician's desk reference texts, medication texts, and/or any other source of information that may be pertinent to the physical training of a user for a particular athletic event or course.

The user performance evaluation module 126 evaluates the activity and/or health monitoring data obtained from the various sources to correlate observed stress/strain and/or low performance or weaknesses with types of motions used at various portions of the training course. The user performance evaluation module 126 performs analysis of the user's performance with regard to both activities and health, at various points along the training course to identify characteristics of the training course that cause excessive stress or strain on the user, cause the user to perform less sufficiently, or the like. The indications of weakness in performance, e.g., stress or strain on the user, or the like, may be determined from comparison of the user's previous performance on other training courses, in previous athletic events where performance data was collected and stored, or the like. In some illustrative embodiments, the user's performance data for the present training course may also be compared to other persons that have trained on a similar training course, performance data for persons that have engaged in the athletic event or race course that the user is training for, or the like. In comparing to other persons, the user's characteristics may be used to identify a pool or group of other persons having similar characteristics and for which performance data has been obtained and stored, e.g., persons having similar demographics, similar health/physical attributes, or the like.

These types of motions determined to cause stress, strain, or insufficient performance, as well as other areas of weakness or insufficient performance with regard to both health and activity capabilities of the user, may then be used by the personalized training module 128 to identify exercises or training regimens that the user may implement to strengthen the user's capabilities in these areas of weakness or insufficiency in performance with regard to specific elements of the training course in question and thus, the ultimate course or athletic event. These training regimens or exercises may comprise both training regimens and exercises with regard to the real world physical training course, exercises and/or training activities performed in a gym or with more stationary gym equipment, exercises and/or training activities the user can perform off the training course and outside of a gym environment, and/or the like. These training regimens and/or exercises may take into account the physical condition of the user as determined from the health information, the user's current physical capabilities based on the health information, and the like. The determination of the training regimen and exercises may be based on resource information of the corpus 106 that identify training activities and exercises that result in increased performance with regard to particular areas of weakness or insufficient performance. For example, resource information of the corpus 106 may indicate how to increase strength in a given area of the body after an injury, increase strength when an area of the body is weakened through repetitive stress injuries, disuse, etc. This resource information may come from electronic documentation of the corpus 106 representing knowledge in physical therapies used by physical therapists, doctors, astronauts, and the like.

In some cases, a new analysis of the geographical area in the geographical region specified by the user may be performed to identify portions of the geographical area that have characteristics that will assist the user in strengthening the areas of weakness or insufficiency in performance. For example, if it is determined that the user seems to have difficulty on hilly terrain and needs to increase the lung capacity, endurance, and/or strength with regard to hilly terrain, then the training course may be modified to emphasize hilly areas that will assist the user in building up the user's performance with regard to hilly areas. Moreover, the geographical region may be analyzed to identify other portions of geographical areas that may not have been previously present in the training course, to thereby add those portions to the training course to emphasize hilly areas as part of the training course. These additions may also replace other portions in the training course for which the user has shown sufficient performance. Thus, a modified training course may be generated in addition to, or in replacement of, the training regimens and/or exercises mentioned above.

The training regimen, the exercises, and/or the modified training course may be output to the client computing device 110 and/or the health/activity monitoring device 130 for implementation by the user to continue or focus their training on the areas where the cognitive system 100 has determined that the user exhibits weakness or insufficient performance. The output of the training regimen, exercises, and/or modified training course may further identify the reasons for the various elements of the output, e.g., the particular areas of weakness or insufficient performance identified by the cognitive system and the way in which the elements of the training regimen, exercises, and/or modified training course will improve those areas if performed properly.

It should be appreciated that this process may be repeated such that a continuous personalized training is obtained until the user discontinues the process. Thus, the user's performance on the modified training course may be monitored and the process repeated to further modify the training course and/or provide other training regimens or exercises. The cognitive system 100 may also maintain in association with an identifier of the user and the planned course or athletic activity, the original training course generated by the cognitive system 100 for periodic evaluation of the user while training. That is, periodically, the cognitive system 100 may send an output to the client computing device 110 and/or health/activity monitoring device 130 to inform the user that they should try the original training course again so as to see where the user has improved in performance. The cognitive system 100 may repeat the above described functions to determine how the user should continue the training in view of their new physical performance on the training course.

Thus, the illustrative embodiments provide a cognitive system for providing personalized training recommendations to a user that are based on an individual assessment of the user's performance with regard to a training course that emulates the characteristics of a planned course or athletic event. The personalized training recommendations may include identifying a training regimen, exercises, and/or a modified training course to assist the user in strengthening their performance in areas of weakness or insufficient performance identified by the cognitive system with regard to the user's health and activity and the characteristics of the training course, and ultimately the planned course or athletic event emulated by the training course.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p° computer system, running the Advanced Interactive Executive) (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

As noted above, the data processing system 200 may be employed to implement a cognitive system 100 that is augmented to include the personalized training recommendation engine 120. As such, the data processing system 200 provides hardware and/or specialized software executing on the hardware, that implement this personalized training recommendation engine 120. The personalized training recommendation system operates to receive a request from a user to generate a personalized training regimen for a specified athletic event or planned course. The personalized training recommendation engine 120 identifies event and/or planned course information associated with the specified athletic event or planned course, such as physical features, geographical and/or environmental characteristics, and the like. The personalized training recommendation engine 120 identifies user information associated with the user, such as health and/or activity information including demographic information, previous performance information, general medical information, and the like. The personalized training recommendation engine 120 utilizes the event or planned course information and the user information, to identify a set of geographical areas within a specified geographical region that emulate characteristics associated with the specified athletic event or planned course within a predetermined tolerance threshold. Responsive to identifying more than one geographical area that emulates the characteristics of portions of the planned course or athletic event, the personalized training recommendation engine 120 selects from the more than one geographical areas the one that ranks highest to emulating the characteristics of the portion of the planned course or athletic event and provides a higher likelihood of providing a contiguous training course with regard to other selected geographical areas.

The personalized training recommendation engine 120 then generates a training course from the selected geographical areas and presents the training course to the user as the personalized training regimen for use by the user in preparing for the specified athletic event or planned course. The generation of the training course that emulates the characteristics associated with the specified athletic event or planned course may involve identifying, by the personalized training recommendation system 120, a training course that is within a predetermined distance of a location associated with the user, such as a home location, and which has portions that emulate characteristics associated with the portions of the specified athletic event or planned course.

The event information associated with the athletic event or planned course may include one or more of a date of the specified athletic event or planned course, a location of the specified athletic event or planned course, a course map of the specified athletic event or planned course, a terrain associated with the athletic event or planned course, or historical environmental characteristics associated with the location and the date. The user information may include one or more of a performance of the user on past events, age of the user, gender of the user, physical attributes of the user such as weight, height, arm lengths, leg lengths, and the like. The user information may further include historical health information for the user including heart rates, lung capacity, blood pressure, range of motion of various limbs, and the like.

It should be appreciated that the selection of geographic areas may result in a failure to identify geographic areas that exactly match the characteristics of the planned course or athletic event, or even match within the given tolerance. In response to a failure to find geographic areas that exactly match or match within the given tolerance, the personalized training recommendation system 120 may select geographical areas that meet a greatest subset of the characteristics associated with the specified athletic event or planned course. Furthermore, the training course generated may be a combination of the selected one or more geographic areas in which intervening geographic areas are included to provide a contiguous training course.

The personalized training recommendation system 120 may also generate one or more exercises to be performed on one or more pieces of exercise devices to train the user for those characteristics that are not represented in the training course but are characteristics associated with the specified athletic event or planned course. That is, if a training course cannot be generated that includes a representation of a characteristic of the planned course or athletic event, then this characteristic may be replicated using exercise equipment so as to allow the user to still train for this characteristic even though there is no geographical area within the specified geographical region where this characteristic is present.

As noted above, the personalized training recommendation system 120 may also monitor the performance of the user on the training course via wearable sensors and health/activity monitoring systems. The data gathered may be correlated to geographical locations along the training course and the corresponding characteristics of the training course at those geographical locations. This information may be used to identify areas of weakness or insufficient performance of the specific user with regard to the specific training course characteristics. A training regimen, set of exercises, and/or modified training course may then be generated to assist the user in strengthening his/her capabilities with regard to the identified areas of weakness or insufficient performance.

Figure 3A:
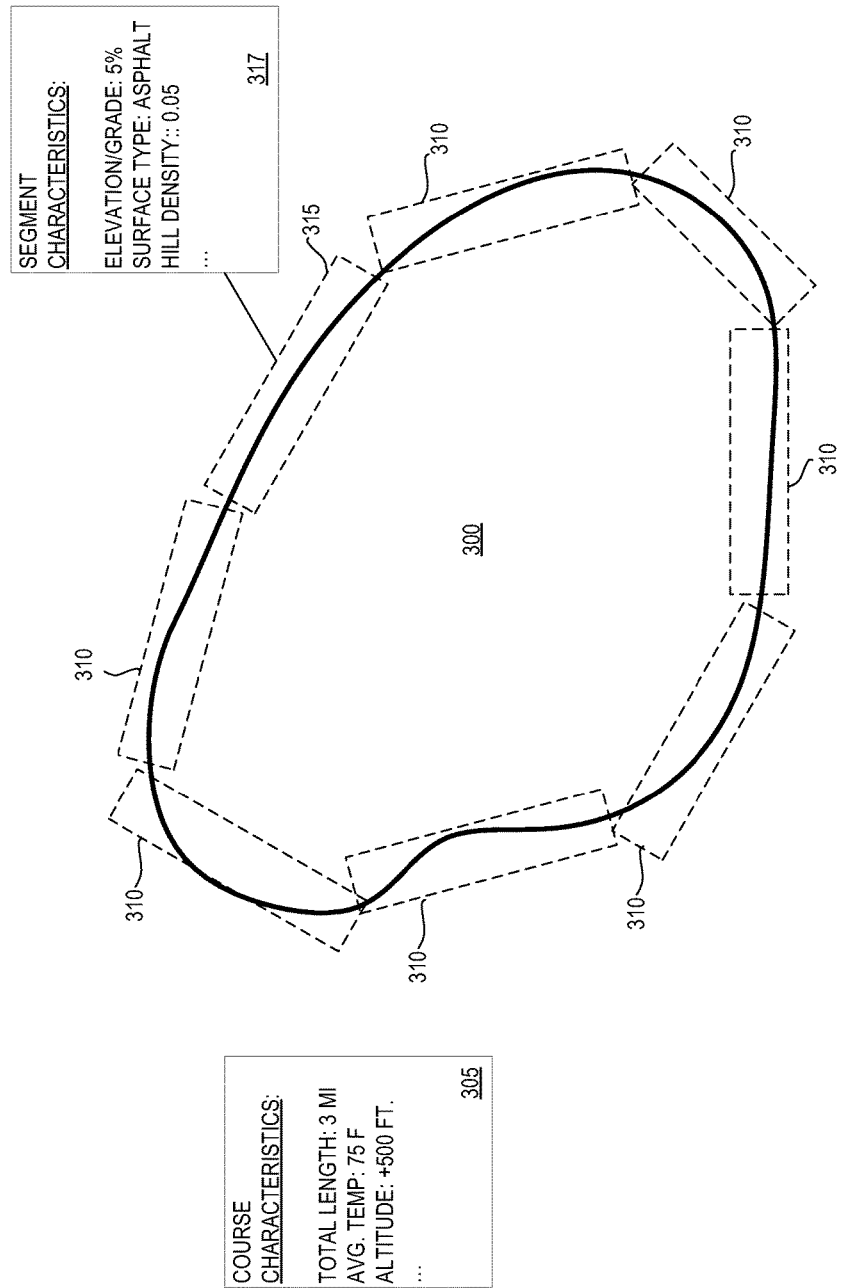
FIGS. 3A-3C depict an example scenario in which a user wishes to train for a specified planned course using the mechanisms of the illustrative embodiments.
Figure 3B:
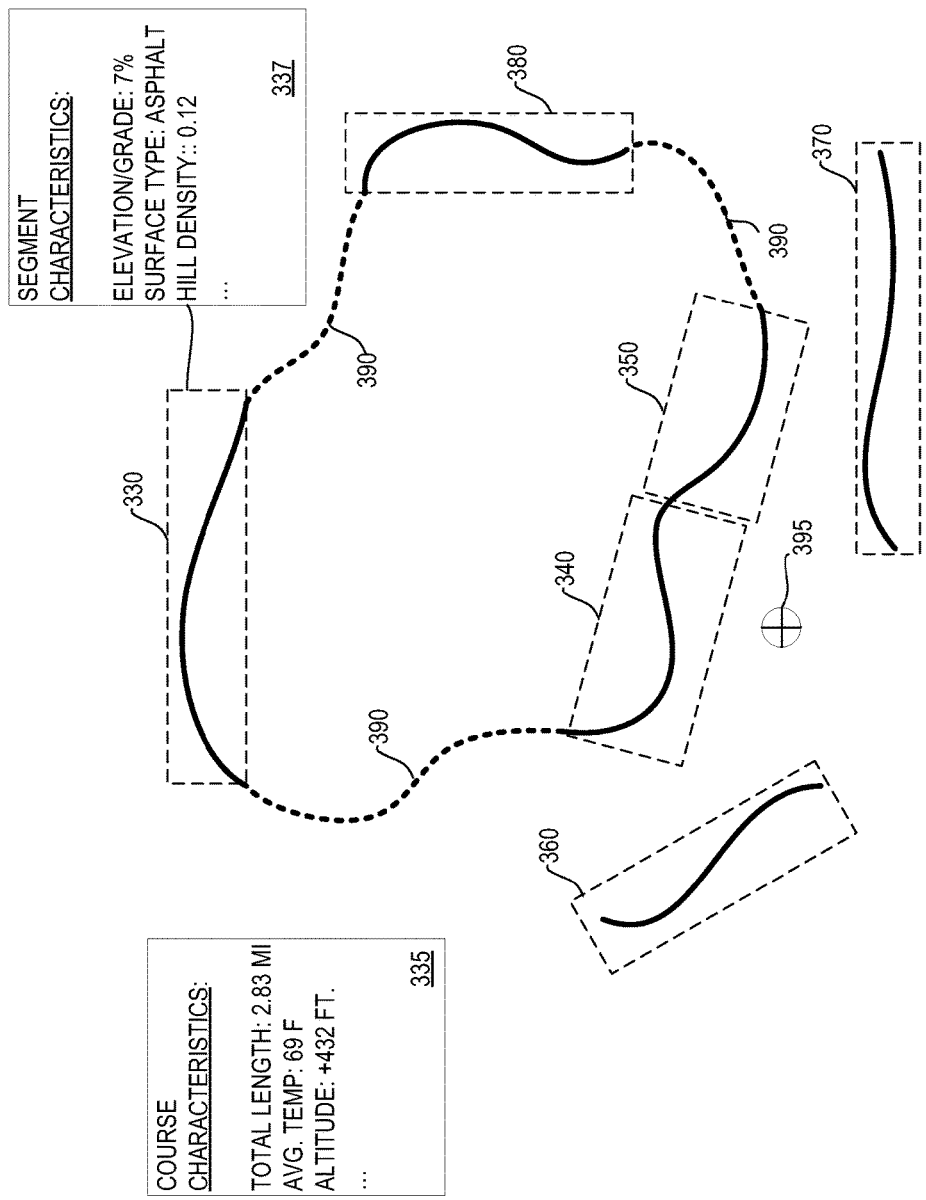
Figure 3C:
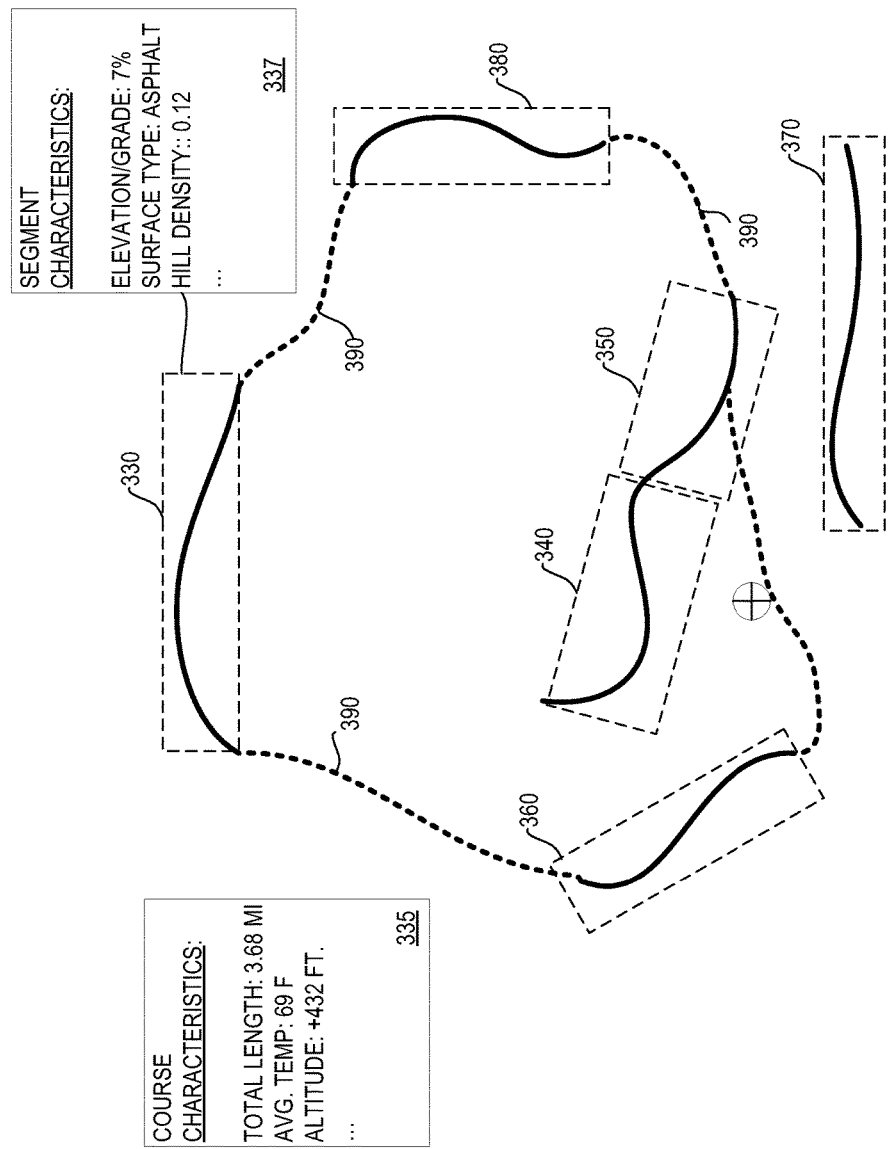

To illustrate the operation of the illustrative embodiments, consider FIGS. 3A-3C which depict an example scenario in which a user wishes to train for a specified planned course using the mechanisms of the illustrative embodiments. FIG. 3A illustrates an example diagram of a race course for which a user wishes to train in accordance with one illustrative embodiment. FIG. 3B illustrates an example diagram of a training course that may be generated from analysis of a geographical area within a specified region based on the characteristics of the race course in FIG. 3A, in accordance with one illustrative embodiment. FIG. 3C illustrates an example diagram of a modification to the training course based on an evaluation of a user's performance on the training course of FIG. 3B relative to other performance indicators of the user in previous training or race events, other persons that have engaged in the race event on the race course of FIG. 3A and/or training course of FIG. 3B, or the like, in accordance with one illustrative embodiment.

As shown in FIG. 3A, and as described previously, a user may submit to the personalized training recommendation engine 120 in FIG. 1 a request to generate a personalized training course for training for a particular specified race course, race event, or the like. The request may further specify a geographical region to be used to generate the training course, and if necessary, may specify characteristics of the race course or event, such as time of year when the race event will occur, time of day, or the like. As noted above, if the race course or race event is not a well-known race course or race event, the request may be generated by a user using their client computing device and, via a user interface, specifying the geographical and environmental conditions of the race event or race course, e.g., tracing the race course or event on a geographical map or the like. For ease of explanation herein, it will be assumed that the race course shown in FIG. 3A is for a well-known race course or race event for which information is already available to the personalized training recommendation engine 120 via the ingestion of a corpus 106 having such information provided therein.

In response to receiving the request from the user, the personalized training recommendation engine 120 retrieves information about the race course and evaluates the planned course using the planned course evaluation module 122, such as by obtaining the physical features and geographical and/or environmental characteristics of the planned course or athletic event from the corpus or corpora 106. For example, the planned course evaluation module 122 may utilize the natural language processing and scoring mechanisms of the request processing pipeline 108 to evaluate electronic documents in the corpus 106 to identify and extract such physical features and geographical and/or environmental characteristics for the planned course or athletic event. The planned course evaluation module 122 may analyze the characteristic information obtained to identify characteristics for the particular time when the user plans to engage in the athletic event or planned course to provide a predicted characteristic for the time when the user plans to engage in the athletic event or planned course. As a result, a collection of characteristics, correlated to geographic locations of the planned course or athletic event, is generated.

For example, as shown in FIG. 3A, the planned course or race course 300 may be broken up into segments 310 for which separate sets of physical, geographical, and/or environmental characteristics are associated, which may differ from one another. For example, segment 315, which is one example of a segment 310 of the planned course or race course 300, has associated characteristics 317 of which examples are elevation or grade, surface type, and hill density, among others. Other segments 310 may have similar types of characteristics but with different values. It should be appreciated that in some cases, some portions 320 of the planned course or race course may not have identifiable characteristics. These characteristics for the segments may be obtained from various sources of data providing that data to the corpus 106, e.g., governmental sources that collect data for geographic regions, weather information sources, athletic event sources that gather such information, or any other source of information pertinent to the physical, geographical, and environment characteristics of the planned course or race course. This information may be analyzed using analysis algorithms or engines of the planned course evaluation module 122 to correlate and calculate values for various characteristics, which may include statistical values for such characteristics, such as averages, medians, distributions, and the like.

In addition, depending on the planned course or race course, characteristics 305 may be identified for the entirety of the planned course or race course. That is, information from the corpus 106 may be identified to identify overall characteristics of the planned course or race course such as the total length, average temperature, average altitude, etc. The characteristics of the overall planned course and the characteristics of individual segments may together be used to identify comparable portions of training courses from the specified region to be evaluated for generation of a training course.

The resulting collection of characteristics for the planned course or athletic event may be provided to the geographic area evaluation module 124. The geographic area evaluation module 124 correlates those characteristics with geographical areas in the geographical region specified by the user, e.g., a geographical region of a 100 mile radius a home location 395 in FIG. 3B in the depicted example. The geographic area evaluation module 124 may perform a similar obtaining of characteristic data and analysis of the characteristic data from the corpus 106 as performed by the planned course evaluation module 122, however the operation is done for the specified geographic region. As a result, a set of characteristics for the geographic region is obtained. The characteristics are associated with geographical locations within the geographic region such that portions 330-380 of the geographic region may be identified that have fuzzy matched characteristics to those of the planned course or athletic event. Hence, a first set of characteristics 317 is generated by the planned course evaluation module 122, and a second set of characteristics 337 is generated by the geographic area evaluation module 124 for each of the portions of the geographic area. It should be appreciated that even though only a single set first and second characteristics 317 and 337 is shown in FIGS. 3A and 3B, each portion or segment may have its own associated set of characteristics whose values may be the same or may differ from other portions or segments.

The geographic area evaluation module 124 then identifies matches, of fuzzy matches between the first set of characteristics 317 (for the planned course or athletic event) and the second set of characteristics 337 (portions of the specified geographic region). The matching may be done with regard to each characteristics and a matching score may be generated based on a combination of degrees of matching of the various characteristics using a matching score calculation function that evaluates these matches quantitatively. The various characteristics and the degree of matching may be weighted according to relative importance of the characteristics to the identification matching portions/segments. The weights may be learned over time, such as via a machine learning process, may be specified by a user, or the like. The weights may likewise be dependent on the particular type of athletic event or planned course, e.g., different characteristic may be more important for a foot race as opposed to a bicycling race, as opposed to a sailing race.

For example, it may be relatively more important to the matching that the elevation of grading of the surface characteristic match more closely between segments of the planned course and portions of the geographical region than the surface type and hill density may be relatively more important than elevation or grading. The score that is calculated based on the matching function may be compared to one or more threshold values that indicate a minimum level of matching required to determine that a portion of the geographical area matches a segment of the planned course or race source. For those portions that have matching scores that meet or exceed the one or more threshold values, the portion may be determined to be a matching portion of the geographical region. It should be appreciated that a variety of different characteristics may be evaluated by the matching function such that different portions of the geographic region may match a different numbers of characteristics for different portions of the planned course or athletic event.

Portions 330-380 of the geographical region, which are similar in characteristics to one or more of the segments 310 of the planned course or athletic event, may be selected to generate a training course for the training of the individual for the planned course or athletic event. The portions of the geographical region may be selected favoring portions that provide a contiguous path or course while also having matching characteristics.

Thus, for example, in the depicted example, portions 330-380 all have matching scores that are sufficient to meet or exceed a threshold value. As shown in FIG. 3B, portions 330, 340, 350, and 380 may be combined to generate contiguous training course with the introduction of other portions 390 that were not portions that were considered to have sufficiently high enough matching scores to be included as matching portions. It should be appreciated that portions 360 and 370 were also candidate matching portions, but were not selected for inclusion in the training course, which may be based on a variety of evaluation factors. For example, the evaluation may determine that the strength of the matching of portions 360 and 370 to segments 310 in the planned course is not sufficiently high, e.g., the matching score of portions 360, 370 is relatively smaller than the portions 330, 340, 350, and 380. Moreover, the evaluation may determine whether there are other portions that match similar individual characteristics but have a higher matching score overall.

Furthermore, the evaluation may evaluate the lengths of the non-matching portions that would be required to generate a contiguous training course with those portions and may select portions so as to minimize the length of the intervening portions that would be required to generate a contiguous training course. In some illustrative embodiments, the selection of matching portions may further evaluate which sets of matching portions make the overall training course characteristics 335 more closely match the overall characteristics 305 of the planned course or race course, e.g., make the total length as close as possible. Various factors and evaluations may be made so as to distinguish which of the matching portions 330-380 to include the training course depending on the desired implementation, and each of these evaluations are intended to be within the spirit and scope of the present invention.

The geographic area evaluation module 124 takes the selected portions 330-350 and 380 of the geographical region of 100 miles radius about the home location 395 and generates a training course for the user based on a combination of the portions 330-350 and 380. This combination of portions 330-350 and may require the concatenation of other portions 390 that do not match or have relatively low levels of matching, with the selected portions 330-350 and 380 so that a contiguous training course is generated that connects the selected portions 330-350 and 380. While FIG. 3B shows this contiguous training course to be a closed loop, this is not required and in fact that training course may be a non-closed training course. The result is a training course that has selected portions 330-350 and 380 of the geographical region that closely match the characteristics of the planned course or athletic event with the potential inclusion of non-matching portions in order to connect the selected portions 330-350 and 380.

The training course is returned by the cognitive system 100 to the user via the user's computing device 110. The training course may be output to the user via the client device 110, health/activity monitoring device 130, or the like, so that the user can perform training and the user's performance during training may be monitored as previously discussed above. The user then performs training on the training course while wearing the wearable sensors 132 and/or health/activity monitoring device 130. The wearable sensors 132 collect health monitoring and/or activity monitoring data which may be provided to the cognitive system 100 via the health/activity monitoring device 130 and client computing device 110, or directly from the health/activity monitoring device 130 via the network 102. The health and activity data obtained from the wearable sensors 132 and/or health/activity monitoring device 130 may be correlated, such as via global positioning system (GPS) capabilities, cellular triangulation, or other location determining capabilities of electronic equipment, with portions 330-350 and 380 of the training course to correlate the user's performance with regard to particular characteristics of the training course. For example, it may be determined that the user's heart rate, breathing rate, overall strain level, time for completion, etc. all are elevated during the user's training in portion 330 which indicates the user's difficulty and/or lack of sufficient performance in portion 330. This information may be correlated with the characteristics of portion 330 indicating the characteristics with which the user is having difficulty or where the user needs to concentrate training for improvement of their performance.

In addition to the wearable health and/or activity monitoring equipment data, as discussed above, the personalize training recommendation engine 120 may obtain data regarding the user's performance during training on the training course from medical personnel, the user himself/ herself, or the like, such as through manual entry of such information, responses to a questionnaire presented after training, evaluation of the user via medical equipment after training on the training course, or any other methodology for obtaining data regarding the user's performance and/or health condition after training. The information gathered after training may also be utilized as a more general performance and/or health data for the training course as a whole. Combined, this information provides an indication of the user's performance during the training on the training course which, when analyzed, will identify areas where the user is weak or has insufficient performance both with regard to the user's capabilities and with the particular characteristics of the training course, and ultimately the planned course or athletic event that the training course emulates.

The performance information obtained from the monitoring device 130 while the user trains on the training course may be correlated with the characteristics of portions of the training course to identify areas where additional training or performance improvement is needed which may then be correlated with exercises, activities, and even other portions of the geographical region which may be useful in assisting the user in improving their performance. Personal data about the user, ingested by the cognitive system 100 from the corpus 106, as well as resource information, may be used by the user performance evaluation module 126 to determine measures of the user's performance and actions to perform to improve that performance where needed. The indications of weakness in performance may be determined from comparison of the user's previous performance on other training courses, in previous athletic events where performance data was collected and stored, or the like. In some illustrative embodiments, the user's performance data for the present training course may also be compared to other persons that have trained on a similar training course, performance data for persons that have engaged in the athletic event or race course that the user is training for, or the like.

The determinations regarding stress, strain, or insufficient performance made by the user performance evaluation module 126 may then be used by the personalized training module 128 to identify exercises or training regimens that the user may implement to strengthen the user's capabilities in these areas of weakness or insufficiency in performance with regard to specific elements of the training course in question and thus, the ultimate course or athletic event. In some cases, a new analysis of the geographical region specified by the user may be performed to identify portions 360 and 370 of the geographical region that have characteristics that will assist the user in strengthening the areas of weakness or insufficiency in performance. For example, portion 360 may comprise similar grade or elevation characteristics to portion 330 with which the user has had difficulty or insufficient performance. By adding in portion 360 to the training course, either in addition to or in replacement of other portions, such as portions for which the user provides sufficient performance, the training course is modified to emphasize an area of weakness or insufficient performance of the user. Thus, when the user trains using the modified training course, as shown in FIG. 3C, the user is trained more heavily with regard to steeper elevations or gradings than the original training course and thereby strengthens the user with regard to those course characteristics.

The training regimen, the exercises, and/or the modified training course may be output to the client computing device 110 and/or the health/activity monitoring device 130 for implementation by the user to continue or focus their training on the areas where the cognitive system 100 has determined that the user exhibits weakness or insufficient performance. The output of the training regimen, exercises, and/or modified training course may further identify the reasons for the various elements of the output, e.g., the particular areas of weakness or insufficient performance identified by the user performance evaluation module 126 and the way in which the elements of the training regimen, exercises, and/or modified training course will improve those areas if performed properly.

It should be appreciated that FIGS. 3A-3C are only provided as one simplified example. Many modifications to the example depicted in FIGS. 3A-3C may be made without departing from the spirit and scope of the present invention.

Figure 4:
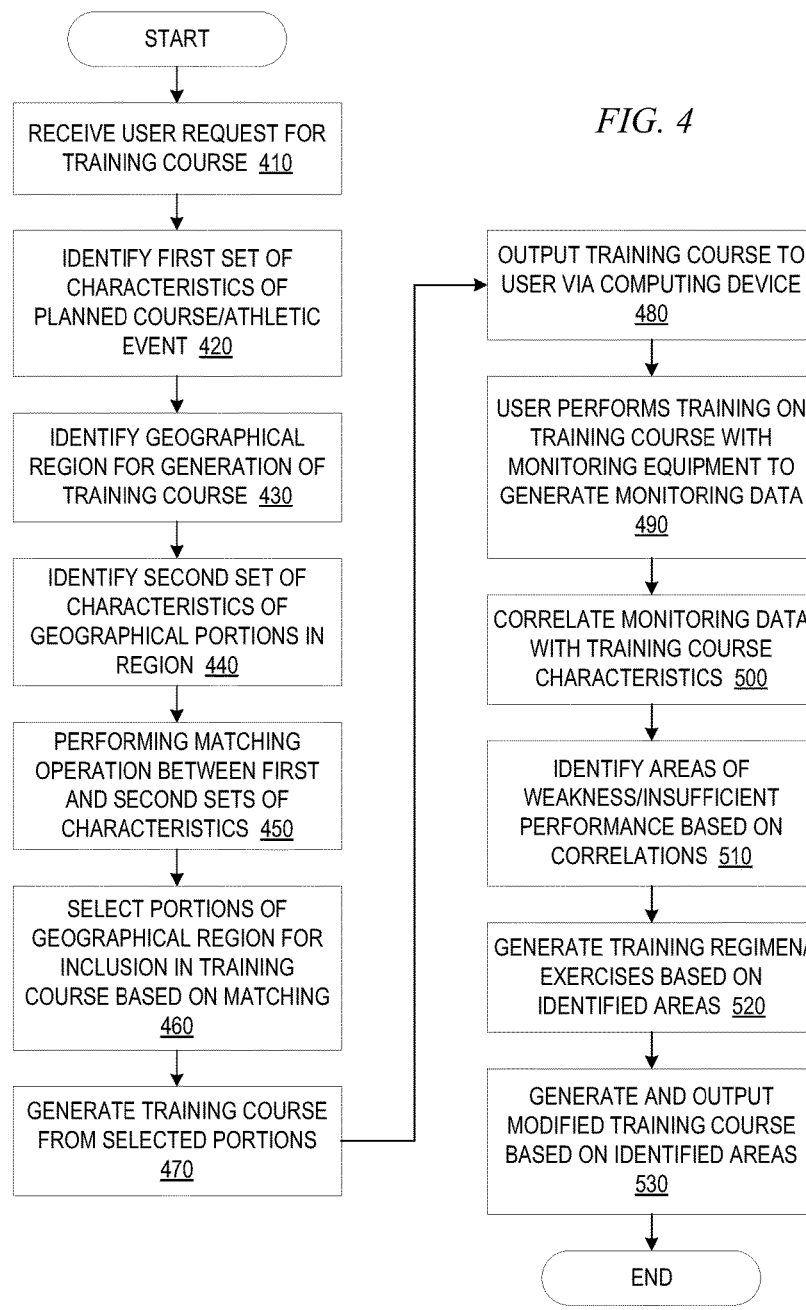
FIG. 4 is a flowchart outlining an example operation of a personalized training recommendation engine in accordance with one illustrative embodiment.

FIG. 4 is a flowchart outlining an example operation of a personalized training recommendation engine in accordance with one illustrative embodiment. The operation outlined in FIG. 4 assumes that the cognitive system implementing the personalized training recommendation engine has ingested one or more corpora of information regarding geographic areas, planned courses and/or athletic events, user health and activity data, and the like. Thus, the operations outlined in FIG. 4 will highlight the operations performed by the personalized training recommendation engine based on the ingested information from the one or more corpora.

As shown in FIG. 4, the operation starts by receiving a user request to generate a training course for a specified planned course or athletic event (step 410). The characteristics of the planned course or athletic event are identified to generate a first set of course characteristics (step 420). The geographical region from which the training course is to be generated is identified from the user request (step 430) and a second set of characteristics for portions, or geographical areas, within the geographical region is generated (step 440). A matching operation is performed to identify portions the geographical region whose characteristics match, within a given tolerance, segments of the planned course or athletic event (step 450). Portions of the geographical region are selected for inclusion in a training course based on a degree of matching of the various characteristics of segments of the planned course/athletic event and the portions of geographical region, as well as the ability to combine the geographical areas together to form a contiguous training course (step 460). A training course is generated from the selected portions, which may include intervening portions that are included to provide a contiguous training course (step 470). The training course is then output to the user via a client computing device (step 480).

The user then performs training on the training course while wearing monitoring equipment to monitor the user's health metrics and activity during the training (step 490). The monitored data is provided to the personalized training recommendation engine which correlates the monitored data with portions of the training course and the characteristics of the training course at these portions (step 500). Based on the correlation, areas of weakness or insufficient performance are identified (step 510) and a training regimen and/or exercises to increase the user's strength in these areas of weakness or insufficient performance are generated and output to the user (step 520). In addition, a modified training course that includes areas where the user's weakness or insufficient performance are prevalent may be generated and output to the user as a suggested modified training course (step 530). The operation then terminates. It should be appreciated that while FIG. 4 shows the operation terminating, the operation may be repeated for continuous training and refinement of the personalized training of the user for the specified planned course or athletic event.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer program product comprising a computer readable storage medium having a computer readable program stored therein, wherein the computer readable program, when executed on a computing device, causes the computing device to:

receive a request from a client computing device associated with a user, the request being to generate a personalized training regimen for a specified athletic event occurring at a future time;

extract, by a cognitive computing system, event information comprising at least one of physical features or environmental features of one or more geographical segments of the specified athletic event based on an ingestion of first data regarding the specified athletic event by the cognitive computing system and generation, by the cognitive computing system, of a first set of features corresponding to the specified athletic event extracted from the ingested first data;

identify, by the cognitive computing system, based on the event information, geographical region information from a knowledge base, for one or more portions of a geographical region within a specified geographical range of a home location associated with the user, wherein the one or more portions approximate at least one of the physical features or environmental features of the one or more geographical segments associated with the specified athletic event within a predetermined tolerance, wherein the identification of the geographical region information is based on a generation, by the cognitive computing system, of a second set of features comprising at least one of physical features or environmental features corresponding to the one or more portions of the geographical region extracted from the ingested second data, and a cognitive comparison of the first set of features and the second set of features using machine learning logic that learns weights associated with different types of features through a machine learning process and applies the weights to the different types of features present in the second set of features via one or more functions to score the one or more portions of the geographical region;

generate, by the cognitive computing system, a training course at least by combining a selected set of the portions of the geographical region based on an evaluation, by the cognitive computing system, of a level of matching, for each portion of the geographical region in the set of portions, based on the scores associated with the one or more portions of the geographical region generated by the machine learning logic; and transmit, by a personalized training recommendation engine, the generated training course to the client computing device for presentation to the user as the personalized training regimen for use by the user in preparing for the specified athletic event.

2. The computer program product of claim 1, wherein the event information includes one or more of a date of the specified athletic event, a location of the specified athletic event, a course map of the specified athletic event, a terrain associated with the course, or historical environmental characteristics associated with the location and the date.

3. The computer program product of claim 1, wherein the computer readable program further causes the computing device to:

monitor, via communication with a wearable health or activity monitoring device associated with the user, performance of the user during training on the generated training course to generate performance data;

determine areas of weakness or insufficient performance by the user on the training course based on an evaluation of the performance data; and correlate the areas of weakness or insufficient performance with characteristics of corresponding portions of the training course.

4. The computer program product of claim 3, wherein the computer readable program further causes the computing device to:

correlate the areas of weakness or insufficient performance, the characteristics of corresponding portions of the training course, and one or more exercises to be performed on one or more pieces of exercise devices to train the user for those characteristics of the corresponding portions of the training course; and present an output to the user to inform them of the areas of weakness or insufficient performance, the characteristics of the corresponding portions of the training course, and the one or more exercises to be performed.

5. The computer program product of claim 4, wherein correlating the areas of weakness or insufficient performance, the characteristics of corresponding portions of the training course, and one or more exercises to be performed further comprises:

correlating the areas of weakness or insufficient performance with types of motions used at the corresponding portions of the training course; and correlating the types of motions with the one or more exercises to be performed on one or more pieces of exercise devices to train the user.

6. The computer program product of claim 3, wherein the computer readable program further causes the computing device to:

modify the training course to include one or more other portions of the geographical region, not previously in the set of portions, based on the correlation of areas of weakness or insufficient performance with characteristics of corresponding portions of the training course, to thereby generate a modified training course.

7. The computer program product of claim 6, wherein the one or more other portions are one or more other portions that have at least one similar characteristic to the characteristics of the corresponding portions of the training course for which the user has shown a weakness or insufficient performance.

8. The computer program product of claim 6, wherein modifying the training course further comprises modifying the training course to include other portions of the geographical region, not previously in the set of portions, and which do not match characteristics of the one or more geographical segments of the specified athletic event, but have at least one of physical features or environmental features that will assist the user in strengthening their performance with regard to the identified areas of weakness or insufficient performance.

9. The computer program product of claim 1, wherein the computer readable program further causes the computing device to generate the training course at least by concatenating the selected set of portions with other non-selected intervening portions between selected portions to form a contiguous training course.

10. The computer program product of claim 1, wherein the request specifies a temporal criterion for the specified athletic event, and wherein a cognitive computing system performs a cognitive computing analysis of a corpus of information to predict at least one of physical features or environmental characteristics of the specified athletic event corresponding to the temporal criterion specified in the request.

11. An apparatus comprising:

a processor; and a memory coupled to the processor, wherein the memory comprises instructions which, when executed by the processor, cause the processor to:

receive a request from a client computing device associated with a user, the request being to generate a personalized training regimen for a specified athletic event occurring at a future time;

extract, by a cognitive computing system, event information comprising at least one of physical features or environmental features of one or more geographical segments of the specified athletic event based on an ingestion of first data regarding the specified athletic event by the cognitive computing system and generation, by the cognitive computing system, of a first set of features corresponding to the specified athletic event extracted from the ingested first data;

identify, by the cognitive computing system, based on the event information, geographical region information from a knowledge base, for one or more portions of a geographical region within a specified geographical range of a home location associated with the user, wherein the one or more portions approximate at least one of the physical features or environmental features of the one or more geographical segments associated with the specified athletic event within a predetermined tolerance, wherein the identification of the geographical region information is based on a generation, by the cognitive computing system, of a second set of features comprising at least one of physical features or environmental features corresponding to the one or more portions of the geographical region extracted from the ingested second data, and a cognitive comparison of the first set of features and the second set of features using machine learning logic that learns weights associated with different types of features through a machine learning process and applies the weights to the different types of features present in the second set of features via one or more functions to score the one or more portions of the geographical region;

generate, by the cognitive computing system, a training course at least by combining a selected set of the portions of the geographical region based on an evaluation, by the cognitive computing system, of a level of matching, for each portion of the geographical region in the set of portions, based on the scores associated with the one or more portions of the geographical region generated by the machine learning logic; and transmit, by a personalized training recommendation engine, the generated training course to the client computing device for presentation to the user as the personalized training regimen for use by the user in preparing for the specified athletic event.

12. The apparatus of claim 11, wherein the event information includes one or more of a date of the specified athletic event, a location of the specified athletic event, a course map of the specified athletic event, a terrain associated with the course, or historical environmental characteristics associated with the location and the date.

13. The apparatus of claim 11, wherein the instructions further cause the processor to:

monitor, via communication with a wearable health or activity monitoring device associated with the user, performance of the user during training on the generated training course to generate performance data;

determine areas of weakness or insufficient performance by the user on the training course based on an evaluation of the performance data; and correlate the areas of weakness or insufficient performance with characteristics of corresponding portions of the training course.

14. The apparatus of claim 13, wherein the instructions further cause the processor to:

correlate the areas of weakness or insufficient performance, the characteristics of corresponding portions of the training course, and one or more exercises to be performed on one or more pieces of exercise devices to train the user for those characteristics of the corresponding portions of the training course; and present an output to the user to inform them of the areas of weakness or insufficient performance, the characteristics of the corresponding portions of the training course, and the one or more exercises to be performed.

15. The apparatus of claim 14, wherein correlating the areas of weakness or insufficient performance, the characteristics of corresponding portions of the training course, and one or more exercises to be performed further comprises:

correlating the areas of weakness or insufficient performance with types of motions used at the corresponding portions of the training course; and correlating the types of motions with the one or more exercises to be performed on one or more pieces of exercise devices to train the user.

16. The apparatus of claim 13, wherein the instructions further cause the processor to:

modify the training course to include one or more other portions of the geographical region, not previously in the set of portions, based on the correlation of areas of weakness or insufficient performance with characteristics of corresponding portions of the training course, to thereby generate a modified training course.

17. The apparatus of claim 16, wherein the one or more other portions are one or more other portions that have at least one similar characteristic to the characteristics of the corresponding portions of the training course for which the user has shown a weakness or insufficient performance.

18. The apparatus of claim 16, wherein modifying the training course further comprises modifying the training course to include other portions of the geographical region, not previously in the set of portions, and which do not match characteristics of the one or more geographical segments of the specified athletic event, but have at least one of physical features or environmental features that will assist the user in strengthening their performance with regard to the identified areas of weakness or insufficient performance.

19. The apparatus of claim 11, wherein the instructions further cause the processor to generate the training course at least by concatenating the selected set of portions with other non-selected intervening portions between selected portions to form a contiguous training course.

20. The apparatus of claim 11, wherein the request specifies a temporal criterion for the specified athletic event, and wherein a cognitive computing system performs a cognitive computing analysis of a corpus of information to predict at least one of physical features or environmental characteristics of the specified athletic event corresponding to the temporal criterion specified in the request.

* * * * *